United States Patent [19]

Fine et al.

[11] 3,996,009

[45] Dec. 7, 1976

[54] SPECIFIC COMPOUND DETECTION SYSTEM

[75] Inventors: David H. Fine, Framingham; David P. Lieb, Lexington, both of Mass.

[73] Assignee: Thermo Electron Corporation, Waltham, Mass.

[22] Filed: Sept. 17, 1975

[21] Appl. No.: 614,100

[52] U.S. Cl. .......................... 23/254 R; 23/232 C; 23/253 PC; 73/23.1
[51] Int. Cl.² ........................................ G01N 31/08
[58] Field of Search ... 23/230 PC, 253 PC, 232 RC, 23/254 R, 255 R; 73/23.1; 55/386, 67

[56] References Cited

UNITED STATES PATENTS

| 3,304,159 | 2/1967 | Hinsuark | 23/253 PC |
| 3,403,978 | 10/1968 | Favre | 23/230 PC |
| 3,647,387 | 3/1972 | Benson et al. | 23/232 R |
| 3,718,429 | 2/1973 | Williamson | 23/232 R |
| 3,746,513 | 7/1973 | Warnick et al. | 23/230 PC |
| 3,847,546 | 11/1974 | Paul | 23/253 PC |
| 3,877,875 | 4/1975 | Jones et al. | 23/230 PC |

OTHER PUBLICATIONS

C. H. Bamford J. Chem. Soc. pp. 12–17, (1939).

*Primary Examiner*—R.E. Serwin
*Attorney, Agent, or Firm*—James L. Neal

[57] ABSTRACT

Apparatus for detecting the amount of a specific compound in a sample. The apparatus comprises, in combination, a gas chromatograph, a cold trap and a specific gas detector. The cold trap includes means to cool the gas passing therethrough to a predetermined pressure therein, whereby gaseous effluent from the trap substantially consists of the specific gas and an inert gas.

2 Claims, 6 Drawing Figures

SPECIFIC COMPOUND DETECTION SYSTEM

CROSS-REFERENCE TO RELATED APPLICATIONS

The subject matter of this application is related to U.S. application Ser. No. 329,949, and further to U.S. application Ser. Nos. 614,099, 614,101, 614,286, and 614,287, filed on even date herewith by David H. Fine; Messrs. Fine and Rounbehler and Messrs. Fine, Lieb and Rounbehler, respectively.

BACKGROUND OF THE INVENTION

This application relates to specific compound detection systems, and more particularly to systems incorporating gas chromatography and specific gas detection techniques.

In general, prior art specific compound detection systems incorporating gas chromatography and specific gas detection techniques face severe limitations in sensitivity and specificity due to the presence of trace contaminants and carrier gas which interfere with the detection of the specific gas. Accordingly, much care has been required in the selection of appropriate carrier gases and, of course, for particular cases, suitable gases are not available. Furthermore, with respect to contaminants, elimination techniques have been of limited effectiveness. The above problems have been particularly evident in the detection of N-nitros compounds.

N-Nitroso compounds are among the most carcinogenic compounds presently known. A single part per million dose may suffice to produce tumors. These compounds have been found in trace quantities in many materials which are taken internally by humans, such as artificial food additives and tobacco smoke. In addition, they may be formed in vivo by internally taking the chemical precursors. In the continuing research into tumor producing substances, N-nitroso compounds are compounds which require study and for which tolerable levels of human consumption need to be determined. As of yet, such levels have not been adequately determined. This is due, at least in part, to the difficulty in measuring the quantity of N-nitrosoamine compounds in particular samples.

One prior method of N-nitroso compound measurement is to heat the N-nitroso compound with hydrogen to convert the nitrogen in the N-nitroso compound to ammonia. The resulting ammonia may then be detected. The major disadvantage of this method is amines and amino acids and other nitrogen fragments are also converted to ammonia and are difficult to distinguish from the ammonia produced by the N-nitroso compounds. This problem may be partly, but only partly, overcome by prior separation on a gas chromatograph column. Even then, identification of the ammonia resulting from converted N-nitroso compounds must be confirmed by high sensitivity mass spectrometry. The results of such a process are very difficult and time consuming to obtain.

Another method which has been tried involves dissolving a sample in a solvent to which nitric oxide dyes are added. Exposure to ultra violet light produces a color change. The color change was measured to provide a reading of N-nitrosoamine content. The method provided very little success. One reason is that other materials which commonly occur in samples also produce color change and thereby erroneous readings. One such other material is furfural.

SUMMARY OF THE INVENTION

An apparatus and method for detecting the N-nitroso compound content in specific samples is provided. N-nitroso compounds have the general formula:

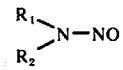

wherein $R_1$ and $R_2$ are the same or different organic radicals, including those radicals which together with the non-nitroso N of the above depicted N—NO bond constitute a nitrogen heterocyclic radical. Generally, according to this method, the N—NO bond which is generally the weakest is first selectively broken to release nitric oxide in the gas phase and then the quantity of liberated nitric oxide is measured. The quantity of nitric oxide released is directly related to the N-nitroso compound present. Therefore, measurement of nitric oxide provides an immediate, accurate and direct reading of the N-nitroso compound content of the sample.

According to the present invention, the N—NO bond is broken by adding an amount of thermal energy to the N-nitroso compound molecules in the sample which is just sufficient to break the N—NO bond, but is insufficient to break bonds in other molecules. The N—NO bond in N-nitroso compounds is the weakest bond with strength typically in the range 5 – 12 kcal per mole. In some cases, the bond strength may be as high as 40 kcal per mole, but even this is nearly half the value for most other chemical bonds. The energization of the N-nitroso compound molecule liberates nitric oxide according to the following reaction:

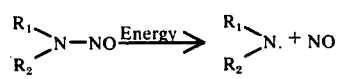

This reaction is accomplished by the non-catalytic pyrolyzation of the N-nitroso compound molecules in the temperature range 300° C to 500° C. The liberated nitric oxide (NO) may be measured directly or it may be oxidized to form nitrogen dioxide and the amount of nitrogen dioxide measured by conventional techniques.

In accordance with one format of the invention, the apparatus comprises a gas chromatography (GC) and an NO detector together with a non-catalytic pyrolyzer. The pyrolyzer includes a chemically inert material configured to provide a cylindrical cross-section flow path for the chromatograph effluent. The pyrolyzer further includes an associated temperature controller for adding thermal energy at a controlled rate so that the flow path is characterized by temperature in the range of 300° C to 500° C.

Alternatively, the apparatus may comprise a liquid chromatograph (LC) in combination with an NO detector together with a non-catalytic pyrolyzer including a similar associated temperature controller. It will be understood that the GC Form utilizes so called gas chromatography wherein the sample (gas or liquid) is introduced into a related inlet port of the column, and the sample material is vaporized. The hot vapors then are separated in the gas chromatograph column. However, the column itself can be either only solids (gas-solid chromatography) or a liquid coated around small solid particles, e.g. a wetted powder (gas-liquid chromatography). It will be further understood that the LC Form utilizes so called liquid chromatography and requires a liquid solvent and a pump, wherein the injection into the column takes place in the liquid phase. The separation can be liquid-liquid, or liquid-solid, e.g. liquids filtering through a packed dry bed (high performance liquid chromatograph or high pressure liquid chromatography).

In both the GC and LC forms of the invention a cold trap may be interposed between the pyrolyzer and the detector so that the cold trap provides a flow path for the pyrolyzer effluent to an input port of the NO detector. The use of cold traps in conjunction with the GC and LC forms of the invention substantially eliminates trace contaminants which might otherwise react in the NO detector and provide erroneous contributions to the N-nitroso compound content signal produced by the detector. In addition, for the GC form, the cold trap may also be configured to remove the carrier gas from the pyrolyzer effluent. Accordingly, both the detection system sensitivity and specificity may be greatly enhanced through the use of such cold traps.

Furthermore, use of cold trap in conjunction with the liquid chromatograph form permits the use of different solvents (including certain organic solvents such as alcohol) to be used in the chromatograph column since the solvents may be selectively removed by the cold trap. Thus, solvent programming may be utilized wherein one solvent is continually displaced in time with a second solvent which is miscible with the first. Solvent programming is a widely used LC technique because the analysis time for a sample can be shortened from hours to minutes. For this form, the column effluent is pyrolyzed in a similar manner to that described above, although in this case there may be a relatively high concentration of pyrolysis products originating from the solvent present in the pyrolyzer effluent. Accordingly, a two stage cold trap arrangement is particularly effective, with the first stage for substantially eliminating the solvent and certain pyrolysis products, and the second stage for eliminating substantially trace contaminants.

In addition, in the LC Form, a carrier gas may be injected into the pyrolyzer at a point near the entry of chromatograph effluent. The carrier gas is generally inert or at least not reactive in the pyrolyzer or in the NO detector. Examples of such gases are argon, helium and nitrogen. The primary function of such carrier gas is to enhance the heat transfer distribution and transport of the column effluent and pyrolysis products between the pyrolyzer input port and the detector.

DETAILED DESCRIPTION OF THE DRAWINGS

Figure 1:
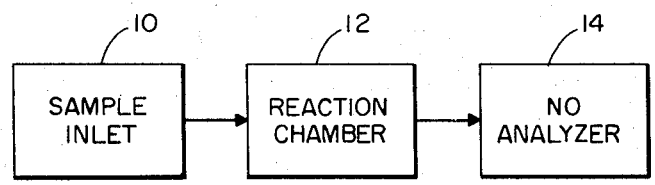
FIG. 1 is a block diagram illustrating apparatus forming a portion of the method of this invention.

The apparatus depicted in FIG. 1 comprises a sample inlet means 10, a reaction chamber 12 and a nitric oxide analyzer 14. A sample to be tested for N-nitroso compound content is injected into the sample inlet means 10. When injected, the sample may be in a condition for immediate receipt into the reaction chamber 12 (e.g., in gaseous state from a gas chromatograph) or it may be in a condition requiring specific preparation for the reaction chamber (e.g., in liquid state from a liquid chromatograph). In circumstances where the sample must be prepared for the reaction chamber 12, there is incorporated with the sample inlet means 10 an appropriate sample preparing apparatus. An example of a sample preparing operation is discussed below.

The reaction chamber 12 subjects the sample to an energy level which is sufficiently high that energy added to the N-nitroso compound molecule will break the N—NO bond. When the N—NO bond is broken nitric oxide is liberated. The nitric oxide is highly stable and has a great resistance to recombining with the remaining fragments of the N-nitroso compound molecule, even though such fragments may be unstable and tend to rearrange into a more stable structure.

The products of the reaction chamber 12 may be fed without further treatment to an appropriate nitric oxide analyzer 14. The nitric oxide analyzer produces a signal proportional to the amount of nitric oxide present and thereby also proportional to the amount of N-nitroso compounds in the sample. Because of the specific amount of thermal energy added in reaction chamber 12, and the specific time relation (established by the chromatograph) of the sample component added to the chamber, this method of measuring N-nitroso compounds in a sample is substantially independent of other materials which may be present in the sample. With this invention, depending on the sensitivity of the particular nitric oxide analyzer chosen, very low N-nitroso compound concentrations can be measured.

Figure 2:
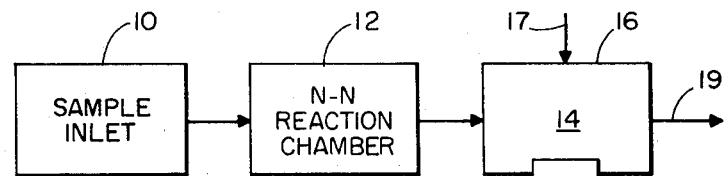
FIG. 2 is a block diagram illustrating a preferred embodiment of the apparatus of FIG. 1.

There will be described in connection with FIG. 2, a preferred embodiment of this invention wherein a solid or liquid sample containing N-nitroso compounds is to be examined. In FIGS. 1 and 2, like numerals are used to designate like parts. Briefly, from the sample inlet 10, the N-nitroso compound containing sample is fed to the reaction chamber 12 which comprises a heated substantially uniform and relatively small diameter conduit for raising the temperature of the liquid sample to a temperature sufficient to break the N—NO bond and vaporize the sample. Vaporization is necessary in this embodiment in addition to the other reasons herein stated because the analyzer includes a chemiluminescent reaction chamber 16 adapted for receipt of vaporized inputs.

It will be understood that the uniform diameter characteristic of the reaction chamber 12 has been found to establish a pressure distribution therein which is particularly effective in promoting the non-catalytic pyrolyzation of the sample. Other forms, such as a relatively large diameter tube having a short restriction, are less effective. The output of the reaction chamber 12 is fed to the nitric oxide analyzer 14 which is of the type described in U.S. patent application, Ser. No. 198,297, filed Nov. 12, 1971, in the name of David P. Lieb, entitled "Fluid Flow Control System". It incorporates the chemiluminescent reaction chamber 16, associated photosensitive device 18 and an ozone inlet 17. When materials from the reaction chamber 12 enter the reaction chamber 16, nitric oxide comes into the presence of ozone and a chemiluminescent reaction results. The intensity of the reaction is a function of the quantity of nitric oxide present. The photosensitive device 18 senses the intensity of the chemiluminescent reaction within the reaction chamber 15 and provides a signal proportional thereto. Materials are discharged from the reaction chamber 16 through an outlet 19.

Figure 4:
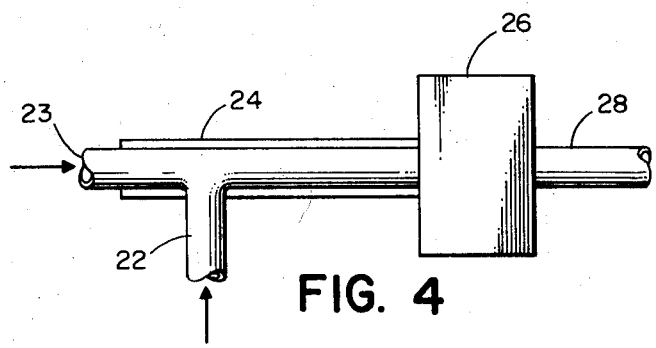
FIG. 4 is a schematic view showing apparatus for performing the method of FIG. 2.

A specific example of the operation of the invention as depicted in FIG. 2, will be set forth in connection with FIG. 4. A liquid sample known to contain N-nitrosodiethylamine is used in conjunction with a liquid chromatograph. The N—NO analyzer is a Model 10-A or Model 12-A NO—NOx analyzer manufactured by Thermo Electron Corporation of Waltham, Massachusetts. The chemiluminescent reaction chamber 26 has a 6-foot long, ⅛ inch diameter, Grade 316 stainless steel tube leading thereto which is heated. The heated tube is represented by numeral 24 in FIG. 4 and constitutes a non-catalytic reaction chamber. A sample inlet port 22 is provided for admitting the sample gases entering the heated tube 24. A carrier gas inlet port 23 is provided for admitting a substantially non-reacting gas, such as nitrogen, argon or helium. The temperature of tube 24 is maintained between 300° C and 500° C.

When the sample is injected into tube 24, the sample flash vaporizes and may be transported without further treatment to the nitric oxide analyzer 26 which provides a reading of the nitric oxide present and thereby of the N-nitrosodiethylamine content of the sample. Generally, the sample has a residence time of 10 seconds or less in tube 24 and tested products are exhausted from chamber 26 through a port 28. This system is virtually interference free since the nitric oxide analyzer is sensitive only to nitric oxide and not to the carrier gas or to other pyrolysis products. Ammonia and various amines which may be formed have no effect upon the detector reading. Additionally, extensive testing has been conducted in relation to many commonly occurring compounds which might be expected to interfere and no interference had been detected, even with test samples such as tobacco tar and chemically preserved food. For this reason, chemical clean-up of the sample, except solvent extraction in cases where a liquid chromatograph is used, is generally unnecessary. With this system, N-nitroso compound concentrations from below 1 ppb on a volume-to-volume basis to pure N-nitroso compound samples have been measured accurately.

Since the chemiluminescent reaction chamber 26 requires a gaseous sample, samples which are originally in a solid form and some which are in a liquid form must be prepared in such a way that the sample and the components of the system performing the method are compatible. For example, without previous chemical preparation, solid or liquid samples may be dissolved in a suitable liquid in which N-nitroso compounds are soluble. Examples of these are dichloromethane, acetone and diethylether. Dilute acids may be used as a solvent provided the N-nitroso compounds reasonably expected to be present in the sample are stable in the acid selected. After the N-nitroso compounds have been dissolved from the sample, the solvent containing the N-nitroso compounds may optionally be partially evaporated to provide a sample having desired volume and concentration characteristics. This solution is then ready for immediate introduction into a liquid chromatograph and the reaction chamber 12. That the solvent may also dissolve other materials is not objectionable.

Figure 3:
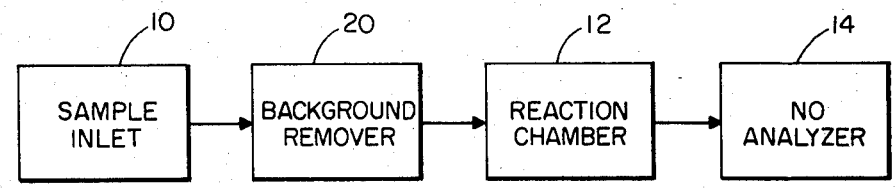
FIG. 3 is a block diagram illustrating a portion of a further embodiment of this invention.

Reference is now made to FIG. 3 wherein there is shown a sample inlet 10, a reaction chamber 12, and a nitric oxide analyzer 14, as in FIG. 1. Additionally, interposed between the sample inlet 10 and reaction chamber 12 is a background removal means 20. The background removal means 20 serves to remove nitric oxide from the sample prior to entry of sample into the reaction chamber 12. For example, if the sample entering the reaction chamber 12 is ambient air or mixed with ambient air, it may contain nitric oxide from that present in the atmosphere. If this nitric oxide is permitted to pass through the reaction chamber 12 and enter the nitric oxide analyzer 14, it will be added to nitric oxide liberated upon the breaking of N-nitroso compound molecules. The ultimate reading will then reflect a summation of nitric oxide present from the two sources. It would then be necessary to determine the extent to which the reading reflected background nitric oxide and nitric oxide released from N-nitroso compounds. Therefore, when background nitric oxide is present, it is preferably removed prior to entry of the sample into the reaction chamber. Many techniques to remove background nitric oxide may be used. Fractional distillation and the use of chromatographic columns of various types are effective.

One suitable operation for removing background nitric oxide involves the passage of the sample, in the gaseous state through a Chromosorb column. That is, the sample is passed through a conduit filled with Chromosorb, a filtering element marketed by Perkin Elmer Corporation of Norwalk, Connecticut, and identified by the Model Nos. 990-5859 through 990-5889. As the fluid passes through the Chromosorb material, nitric oxide is removed. The sample may then be fed to the reaction chamber in a state free of nitric oxides. If the sample contains nitrates and nitrites, these are separated from the N-nitroso compounds by the column with the result that the NO detector produces separate readings for the NO produced by the pyrolysis of the nitrates, nitrites and N-nitroso compounds. Background nitric oxide might also be removed with a molecular sieve column.

The compositions upon which the method of this invention is operable can be any having the formula appearing above. Examples of such compositions follow:

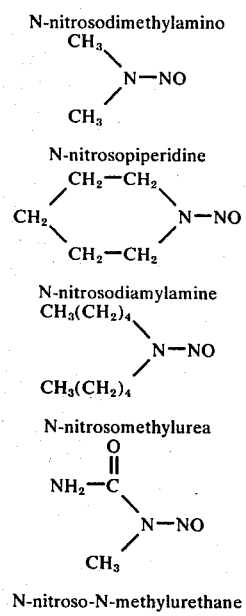

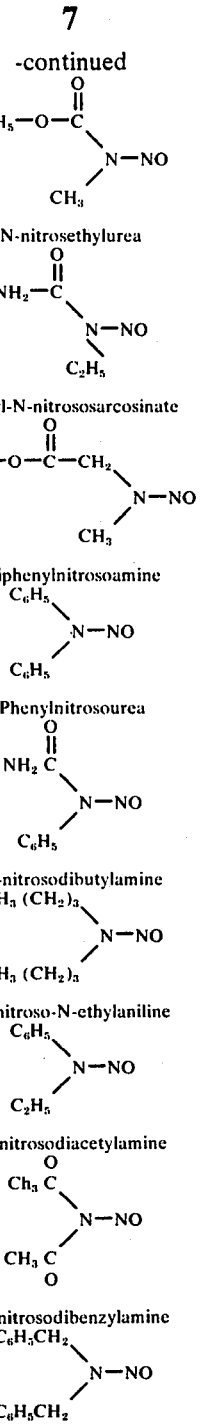

The nitric oxide measuring steps may be by other conventional techniques as well as by the chemiluminescence technique described above. For example, the intensity to the infrared absorption spectrum of the nitric oxide liberated from the N-nitroso compound molecule may be measured. A suitable non-dispersive infrared radiation detection instrument is available from Beckman Instruments, Inc., of Fullerton, California. One suitable model is designated 315-A. Further nitric oxide detection schemes may involve first oxidizing the nitric oxide to produce nitrogen dioxide and then measuring the resulting nitrogen dioxide concentration. In any event, the N-nitroso compound content will be directly proportional to the NO or $NO_2$ present.

The concentration of the nitrogen dioxide may be determined by measuring the intensity of the ultra violet absorption spectrum of the nitrogen dioxide produced. An ultra violet filter photometer, Model 255-A, marketed by Beckman Instruments, Inc., of Fullerton, California, is suitable for this purpose. Alternatively, a mass spectrometer, tuned to the mass of NO, may be utilized as the NO detector.

Figure 5:
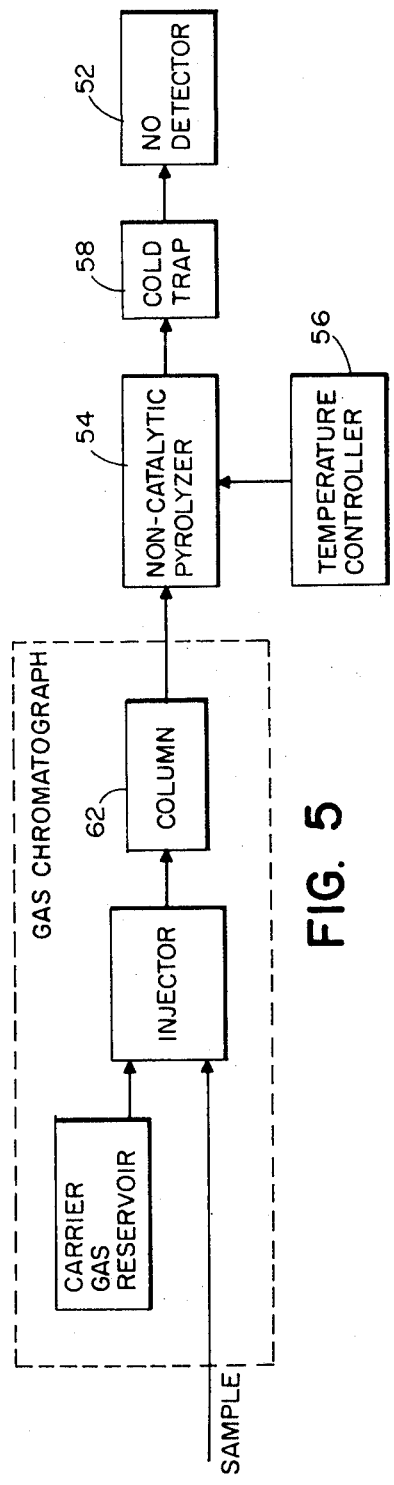
FIGS. 5 and 6 are block diagrams of GC and LC embodiments of the present invention.

FIG. 5 shows a GC embodiment of the present invention comprising a gas chromatograph 50, an NO detector, non-catalytic pyrolyzer 54 and associated temperature controller 56 and a cold trap 58. The gas chromatograph further includes a column 62, injector 64 and a carrier gas reservoir 68. The pyrolyzer 54 and controller 56 together establish a generally cylindrical flow path for the column effluent to the cold trap 58. The interior walls of the pyrolyzer are chemically inert and include a means of establishing a temperature therein in the range of 300° C to 500° C. The interior walls of the pyrolyzer 54 may be formed from quartz, ceramic materials or high temperature borosilicate glass. Since typically used prior art materials do not provide gas tight seals and necessary structural integrity at the specified temperature range.

In the present embodiment, a 0.25 inch outer diameter, 0.070 inch diameter, 2 foot length cylindrical ceramic shell is utilized.

The NO detector 52 may comprise a chemiluminescent ozone reaction detector such as the N—NO analyzer Model 10-A manufactured by Thermo Electron Corporation, Waltham, Massachusetts. In such a system, the input pressure to the pyrolyzer is maintained to be approximately 1 atmosphere and the pressure in the reaction chamber of the NO detector is maintained to be approximately 0.5mm – 20mm Hg.

The cold trap 58 may be one of many forms of the art and in this embodiment, by way of example, may comprise a 0.25 inch copper tube having a 4mm inner diameter and being 18 inches long, with the tube exterior being maintained at or near −150° C but in no event colder than −152° C, so that NO in the trap remains in the gas phase. The gas chromatograph 50 may be one of many known types which provide a flow rate on the order of 4–200 cc/min. The carrier gas may be an inert gas or alternatively may be a relatively inert gas such as nitrogen, or alternatively may be any organic or inorganic vapor, provided the vapor condenses at the cold trap temperature at the cold trap pressure (which is near the detector pressure).

In this GC embodiment, the sample is injected in liquid form, vaporized in the GC column near the input port, and, together with the carrier gas, is driven through the column. The resultant column effluent is injected into pyrolyzer 54 and then pyrolyzed at a temperature substantially in the range 300° C to 500° C. The resultant pyrolyzer effluent is injected into the cold trap 15. At the low temperature and pressure associated with cold trap 58, NO produced by the pyrolyzer passes on to the NO detector 52. In the case where nitrogen, helium or argon is used as a carrier gas, the carrier gas also passes on to the NO detector, although that detector is insensitive to these gases. In the case where an organic vapor, as specified above, is used as a carrier gas, the carrier gas condenses in the cold trap together with pyrolysis products so that only the pyrolyzer-produced NO passes through the cold trap 58 and reaches the NO detector 52.

As noted above, at the temperature ranges established in pyrolyzer 54, the N—NO bond of the N-nitroso compounds is broken with the subsequent release of NO. However, in addition, certain nitrates and nitrites which might be present in the sample also break down at this temperature range to produce NO. Accordingly, one of the functions of the gas chromatograph 50 is to separate the nitroso compounds from any such nitrate or nitrite compounds so that the NO reaching detector 52 which is produced by breakdown of such nitrates and nitrites is separated in time from that produced by the N-nitroso compound pyrolysis reaction.

Figure 6:
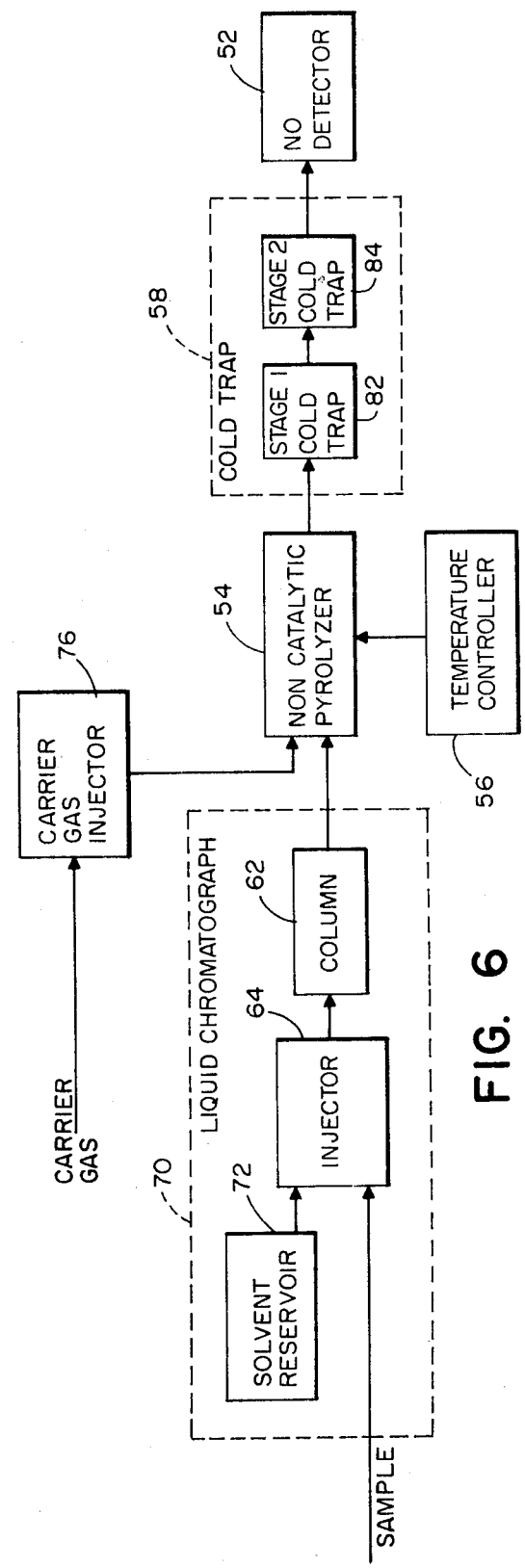

FIG. 6 illustrates an LC embodiment of the present invention utilizing a liquid chromatograph in conjunction with a similar configuration to that embodiment of FIG. 5. Accordingly, in FIG. 6, elements corresponding to elements in FIG. 5 are identified with identical reference numerals.

In FIG. 6, a liquid chromatograph 70 is connected to an NO detector 52 by way of an non-catalytic pyrolyzer 54 and associated temperature control 56 and cold trap 58. The liquid chromatograph 70 includes a solvent reservoir 72, an injector 64 for combining the sample with the solvent and injecting those materials in liquid form into a column 62.

In the embodiment of FIG. 6, the pyrolyzer 54 also has associated injector 76 for injecting a carrier gas into the pyrolyzer. Also in this embodiment the cold trap 58 includes a stage 1 trap 82 and a stage 2 trap 84.

The chromatograph 70 comprises a liquid chromatograph which provides a flow rate in the approximate range 0.1 ml/min. to 6 ml/min. The pyrolyzer 54 and controller 56 may be for example identical to that described above in conjunction with the embodiment of FIG. 5, except that an additional port is located at the input end for injecting a carrier gas by means of injector 76 at injection rates up to 100 cc/min., for example. The particular carrier gas injected may be the same as the gas in conjunction with the embodiment of FIG. 5 and provides a purging and heat transfer function for the pyrolyzer 54, cold trap 58 and detector 52.

The NO detector 52 may be the same detector used in conjunction with the FIG. 5 embodiment.

On this embodiment, the input pressure at pyrolyzer 54 is approximately 1 atmosphere and the pressure at the output of cold trap 58 is on the order of 0.5mm to 20mm Hg.

The two-stage trap arrangement for trap 58 in the present exemplary embodiment includes trap 85 which is substantially identical to that described above in conjunction with the FIG. 5 embodiment, and trap 82 which comprises a 200mm long, 28mm diameter glass tube having its exterior maintained at or near −95° C. With this configuration, the chromatograph solvent is condensed in trap 82 so that the effluent of that trap is substantially solvent free. The trap 84 functions in substantially the same manner as described above in conjunction with FIG. 5 embodiment and condenses contaminents present in the effluent from trap 82 which otherwise might pass on to detector 52 and contribute an erroneous component to the N-nitrosamine content signal produced by detector 52. This particular two-stage trap arrangement for first removing solvent (which is a relatively large quantity for the liquid chromatograph configuration) followed by the second step of removing contaminents before passing NO and carrier gas to the detector, is merely an exemplary arrangement which has been found to be particularly effective. However, alternative cold trap arrangements (such as the utilization of a single −150° C trap) might also be utilized in keeping with the present invention.

It will be understood that with the embodiments of both FIG. 5 and FIG. 6, the N-nitroso compound content of the sample is effectively pyrolyzed in a noncatalytic step in the temperature range 300° C to 500° C, wherein that temperature range the N—NO bond breaking step is accomplished readily without an associated catalyst. As noted above, since in this temperature range, nitrate and nitrite compounds in the sample might also break down to produce NO, and thereby distort the N-nitroso compound content signal produced by detector 52, the chromatograph (either 50 or 70) is primarily utilized to separate in time the application of the nitrate and nitrite compounds from the N-nitroso compounds at the input to the pyrolyzer 54. As a result, the NO detector 52 provides separate output measurement signals for the NO produced by each of these compounds at points in time corresponding to the input injection times into the pyrolyzer 54. It will be further understood, that the cold trap both in FIG. 5 and FIG. 6 embodiments effectively remove other trace contaminents which might produce an erroneous result from the detector 52. In particular with the NO detectors noted above which utilize an ozone reaction, such reactions as certain double and triple bond hydrocarbons with ozone, for example, may produce a luminescence in the infrared which could mask the N-nitroso compound measurement. Accordingly, both the chromatograph and the cold trap improve the specificity and selectivity of the N-nitroso compound detection apparatus.

The present invention has been described in reference to various embodiments. It should be understood that modifications may be made by those skilled in the art without departing from the scope of the invention.

We claim:
1. A gas chromatograph detection system for detecting the amount of predetermined compounds in a sample comprising, in combination:
A. a specific gas detector having an input port and including means for providing a signal representative of the amount of said specific gas injected into said input port,
B. a gas chromatograph having a carrier gas reservoir, a column with an input end and an output end, a means for dissolving said sample in said carrier gas and means for injecting the resulting gas solution into said column at said input end,
C. a cold trap having an input port for receiving a cold trap input gas, and an output port including means for injecting gaseous cold trap effluent into said detector input port, said cold trap input gas consisting of said carrier gas, said specific gas and other compounds in the gaseous state, and said cold trap including means for cooling said cold trap input gas to a relatively low trap temperature at a predetermined trap pressure whereby said gaseous cold trap effluent substantially consists of said specific gas and said carrier gas,
D. chromatograph-cold trap joinder means for receiving gaseous effluent from said output end of said column, for transforming said effluent to said cold trap input gas, and for injecting said cold trap input gas into said cold trap input port, wherein said carrier gas and said specific gas are characterized by a vapor pressure whereby said carrier gas and said specific gas exist only in the gaseous state at said trap temperature and trap pressure, and said other compounds are characterized by a vapor pressure whereby said other compounds exist only in the liquid or solid state at said trap temperature and trap pressure, and wherein further said specific gas detector is relatively insensitive to said carrier gas.

2. The system according to claim 1 wherein said joinder means includes means for adding thermal energy to said column effluent whereby said effluent is transformed to said cold trap input gas.

* * * * *